US00PP35993P2

(12) United States Plant Patent
Lommerse

(10) Patent No.: US PP35,993 P2
(45) Date of Patent: Jul. 9, 2024

(54) ***LEWISIA* PLANT NAMED 'LOCORA3519'**

(50) Latin Name: *Lewisia cotyledon*
Varietal Denomination: LOCORA3519

(71) Applicant: Lommerse Holding B.V., Mariahout (NL)

(72) Inventor: Henry Lommerse, Mariahout (NL)

(73) Assignee: Lommerse Holding B.V., Mariahout (NL)

( * ) Notice: Subject to any disclaimer, the term of this patent is extended or adjusted under 35 U.S.C. 154(b) by 0 days.

(21) Appl. No.: 18/445,637

(22) Filed: Nov. 30, 2023

(30) Foreign Application Priority Data

Dec. 21, 2022 (QZ) ..... PBR 2022/3101

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05)

(58) Field of Classification Search
USPC ..... Plt./263.1
See application file for complete search history.

(56) References Cited

U.S. PATENT DOCUMENTS

PP31,386 P2 * 1/2020 Lommerse ..... A01H 6/00
Plt./263.1

* cited by examiner

*Primary Examiner* — Karen M Redden
(74) *Attorney, Agent, or Firm* — Samuel R. McCoy, Jr.

(57) ABSTRACT

A new and distinct *Lewisia* plant named 'LOCORA3519' which is characterized by a symmetrical and naturally compact rosette of narrowly oblanceolate foliage, with an abundance of vibrant red-purple flowers held in cyme inflorescences above the rosette, and flowering within the first year of growth without vernalization, as well as the stability of these characteristics from generation to generation.

3 Drawing Sheets

Latin name of the genus and species: The Latin name of the genus and species of the novel variety disclosed herein is *Lewisia cotyledon*.

Variety denomination: The inventive variety of *Lewisia* disclosed herein has been given the variety denomination 'LOCORA3519'.

BACKGROUND OF THE INVENTION

Parentage: 'LOCORA3519' is a seedling selection resulting from the open-pollination of a cultivated population of *Lewisia cotyledon* '103510/A' (not patented), a cultivar developed and owned by the inventor. The crossing occurred in approximately April of 2010 at a plant breeding facility in Mariahout, the Netherlands. In the summer of 2012, one plant that resulted from said open-pollination was observed to exhibit improved vigor and flowering in the first year of growth, without the requirement of vernalization. The seedling was isolated for further evaluation in order to confirm the distinctness and stability of the characteristics first observed. Upon confirmation of distinctness and stability, 'LOCORA3519' was selected for commercialization.

Asexual Reproduction: Asexual reproduction of the new cultivar 'LOCORA3519', by way of meristematic tissue culture, was first initiated in June of 2012 at a plant tissue culture laboratory in The Netherlands. The unique features of this cultivar have proven to be stable and true to type, through numerous generations, beginning in 2012.

SUMMARY OF THE INVENTION

The cultivar 'LOCORA3519' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LOCORA3519'. These characteristics in combination distinguish 'LOCORA3519' as a new and distinct *Lewisia* cultivar:

1. 'LOCORA3519' exhibits improved plant vigor with a relatively short, one-year crop cycle as opposed to a two-year crop cycle; and
2. 'LOCORA3519' exhibits narrowly oblanceolate foliage, arranged in a symmetrical, naturally compact rosette that is produced without the aid of plant growth regulators; and
3. 'LOCORA3519' exhibits flowering within the first year of growth, without vernalization; and
4. 'LOCORA3519' exhibits cymes held above the rosette which bear vibrant red-purple flowers; and
5. 'LOCORA3519' exhibits a floriferous bloom habit with flowers present from late June through early August.

BOTANICAL DESCRIPTION OF THE PLANT

Figure 1:
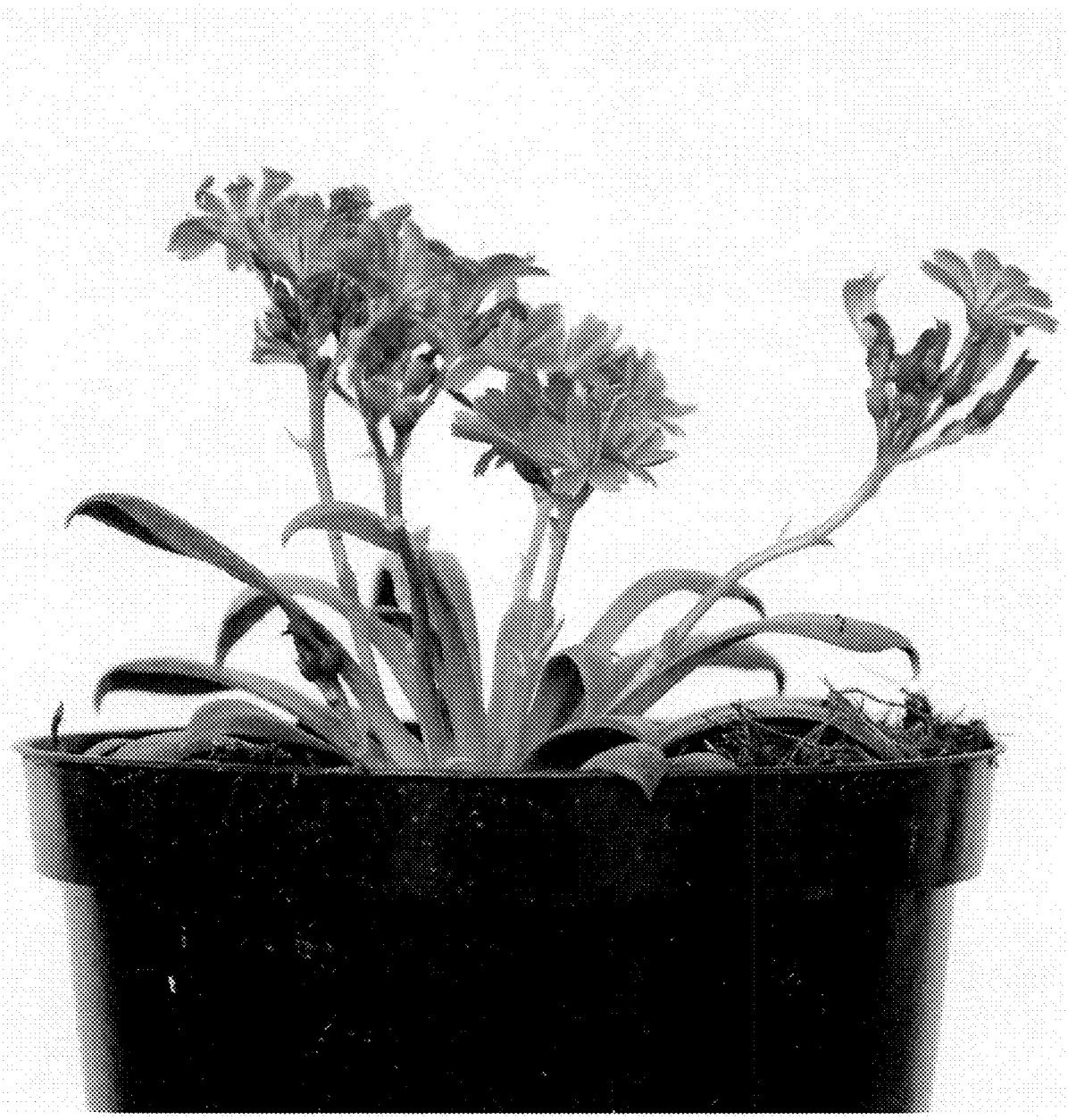
FIG. 1 illustrates, as nearly true as it is reasonably possible to make the same in color photographs of this type, an exemplary plant of 'LOCORA3519' in flower, grown in a greenhouse in Mariahout, The Netherlands. This plant is approximately 12 months old and is shown planted in a 14 cm container.
Figure 2:
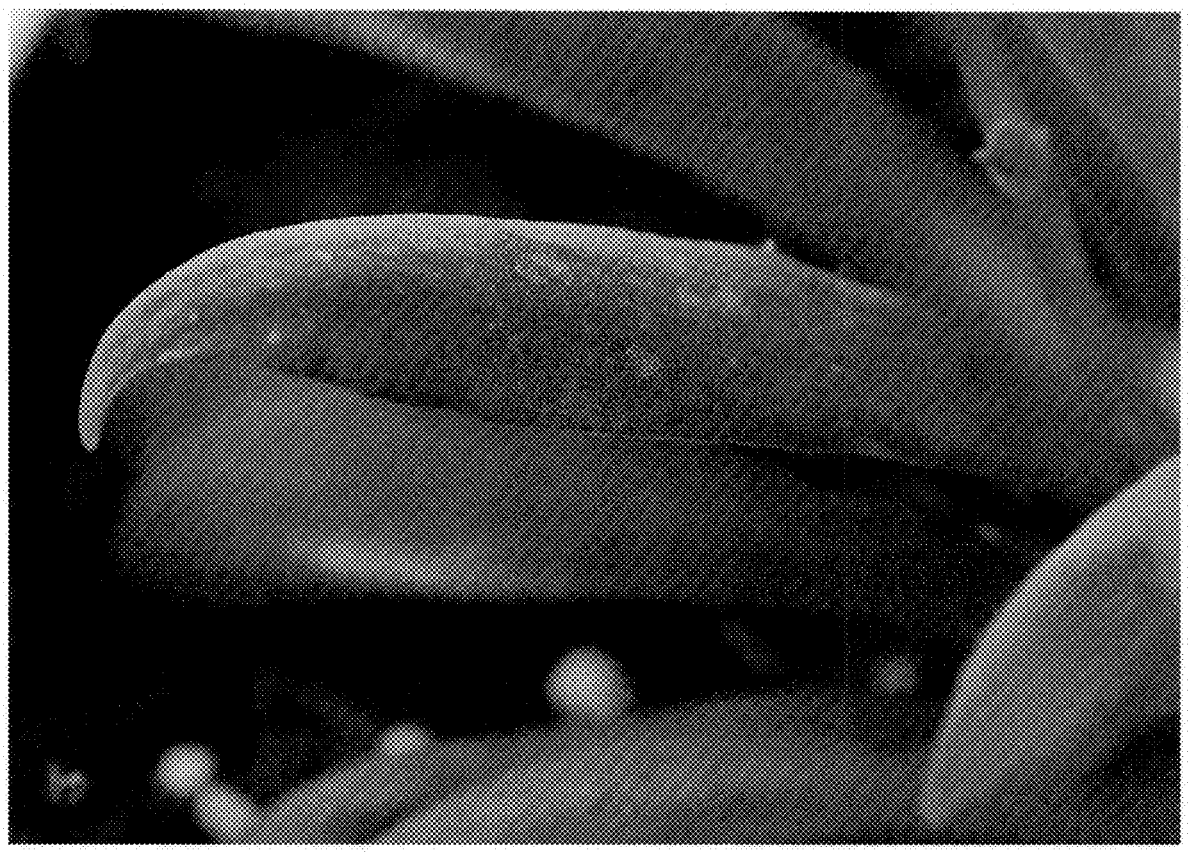
FIG. 2 illustrates, as nearly true as it is reasonably possible to make the same in color photographs of this type, the typical foliage of 'LOCORA3519'.
Figure 3:
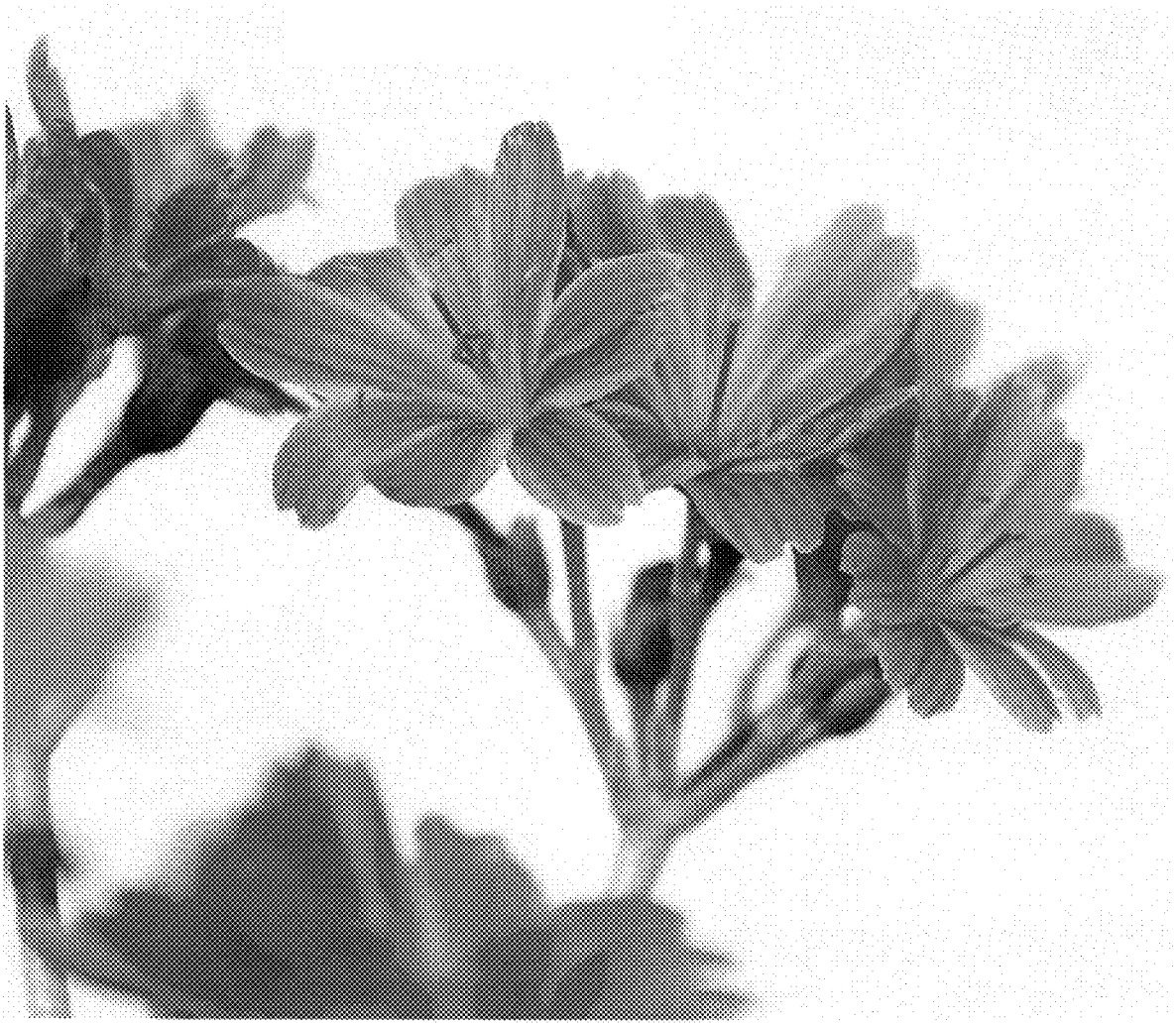
FIG. 3 illustrates, as nearly true as it is reasonably possible to make the same in color photographs of this type, the typical inflorescence of 'LOCORA3519'.

The following observations and measurements made in September of 2023 describe averages from a sample set of six specimens of 12-month-old 'LOCORA3519' plants grown in 14 cm nursery containers at a commercial greenhouse in Mariahout, the Netherlands. Plants were produced under full sun exposure, with minimal subsurface irrigation, no fertilizer application, and no chemical pest and disease control measures. No photoperiodic treatments or artificial light was given to the plants.

Those skilled in the art will appreciate that certain characteristics will vary with older or, conversely, with younger plants. 'LOCORA3519' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'LOCORA3519' and comparisons with the parent plants and closest known comparator are provided below.

Plant description:

*Growth habit*.—Herbaceous evergreen perennial with foliage growing in a non-branched basal rosette and inflorescence carried above the foliar plane.

*Plant profile*.—Flattened.

*Height from soil level to top of foliar plane*.—5.2 cm.

*Height from soil level to top of floral plane*.—9.8 cm.

*Plant spread*.—Average of 15.0 cm.

*Growth rate*.—Relatively fast.

*Plant vigor*.—Vigorous.

*Propagation*.—Type — Meristematic tissue culture. Crop time — Approximately 16 weeks to produce a fully rooted plant in a 12 to 15 cm nursery container.

*Disease and pest resistance or susceptibility*.—Neither resistance nor susceptibility to typical *Lewisia* pests has been observed; lower susceptibility to typical *Lewisia* diseases has been observed.

*Environmental tolerances*.—Adapt to temperatures as high as 40 degrees Celsius and at least as low as negative 12 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosulate.

*Division*.—Simple.

*Attachment*.—Sessile.

*Quantity*.—Approximately 36 leaves per rosette.

*Shape*.—Narrowly oblanceolate.

*Dimensions*.—7.5 cm long, 1.3 cm wide, on average.

*Aspect*.—Convex; slightly revolute; slightly curved downward at the apex.

*Attitude*.—Younger foliage near the center of the rosette is somewhat upright; foliage becomes progressively more relaxed towards the outer whorl of the rosette.

*Apex*.—Abruptly acute to short apiculate.

*Base*.—Narrowly cuneate.

*Margin*.—Entire; not undulated.

*Pubescence, texture and luster of the adaxial surface*.—Glabrous, moderately coriaceous, and glaucous yet moderately glossy.

*Pubescence, texture and luster of the abaxial surface*.—Glabrous, moderately coriaceous, and slightly glossy.

*Color*.—Juvenile foliage, adaxial surface — Yellow-green, nearest to RHS 144A; and transitioning to green towards the apex, nearest to RHS 143A. Juvenile foliage, abaxial surface — Yellow-green, nearest to RHS 146C. Mature foliage, adaxial surface — Green, nearest to RHS NN137B, and fading to a lighter shade of green towards the base, nearest to RHS 143B; epicuticular wax is greyed-green, nearest to RNS 191A. Mature foliage, abaxial surface — Yellow-green, nearest to RHS 146B.

*Venation*.—Pattern — Pinnate. Color, adaxial surface — Main central vein is green, nearest to RHS 143A yet slightly darker; lateral vein coloration is indistinguishable from that of the lamina. Color, abaxial surface — Main central vein is yellow-green, nearest to RHS 145B; lateral vein coloration is indistinguishable from that of the lamina.

Inflorescence:

*Type*.—Axillary cyme.

*Natural flowering season*.—Late June through early August in The Netherlands.

*Bloom habit*.—Floriferous.

*Flowers per inflorescence*.—Average of 13.

*Flowers per plant*.—Approximately 70 open flowers and 8 flower buds.

*Inflorescence height*.—Approximately 10.3 cm, including the peduncle.

*Inflorescence diameter*.—Approximately 4.4 cm.

*Peduncle*.—Attitude — Upright and outward, at an average angle of 30 degrees from vertical. Cross section — Ovoid; somewhat flattened. Dimensions — 7.6 cm long and 0.2 cm wide. Texture — Smooth; glabrous. Luster — Moderately glossy. Strength — Moderately strong. Color — Yellow-green, nearest to a mixture of RHS 146C and 152B, and lightly suffused with greyed-orange towards the distal end, nearest to RHS 172A.

Flower buds:

*Bud shape*.—Oblong.

*Bud dimensions*.—0.8 cm long and 0.35 cm in diameter.

*Bud texture*.—Smooth; glabrous.

*Bud luster*.—Slightly glossy.

*Bud color*.—Immature sepals are yellow-green, nearest to RHS 144B, and immature petals are red-purple, nearest to RHS N66B.

Flower:

*Flower shape*.—Rotate, with two whorls of petals.

*Lastingness*.—Flowers persist for approximately 7 days.

*Persistence*.—Persistent.

*Flower aspect*.—Upright to slightly outward.
*Fragrance*.—Non-fragrant.
*Vertical height*.—Approximately 2.4 cm.
*Diameter*.—Approximately 2.4 cm.
*Depth*.—Approximately 1.0 cm.
*Pedicel*.—Attitude — At an angle of approximately 22.5 degrees to the peduncle. Cross section — Ovoid; somewhat flattened. Dimensions — 0.3 cm long and 0.075 cm wide. Texture — Smooth; glabrous. Luster — Slightly glossy. Strength — Moderately strong. Color — Yellow-green, nearest to RHS 152B.
*Calyx*.—Calyx shape — Cup-shaped; comprised of two oppositely placed sepals. Calyx dimensions — 0.35 cm in diameter and 0.35 cm deep. Sepals — Sepal arrangement — Opposite; not fused. Number of sepals — 2. Dimensions — 0.35 cm long and 0.35 cm wide. Margins — Entire; not undulated. Shape — Short oblong; concaved. Apex — Praemorse. Base — Obtuse. Sepal texture (inner surface) — Smooth; glabrous. Sepal texture (outer surface) — Smooth; glabrous. Sepal luster (inner surface) — Slightly glossy. Sepal luster (outer surface) — Very slightly glossy. Sepal color, when opening (inner surface) — Yellow-green, nearest to in between RHS 144B and 144C. Sepal color, when opening (outer surface) — Yellow-green, nearest to in between RHS 144B and 144C. Sepal color, when fully opened (inner surface) — Yellow-green, nearest to RHS 144C; veined darker, nearest to RHS 146D. Sepal color, when fully opened (outer surface) — Yellow-green, nearest to RHS N148C; veined darker, nearest to RHS N148A.
*Corolla*.—Petals — Quantity — 9. Arrangement — Rotate. Fused or free — Free. Dimensions — Approximately 1.4 cm long and 0.55 cm wide. Shape — Narrowly obovate to oblanceolate. Apex — Emarginate. Base — Cuneate. Aspect — Moderately reflexed. Margin — Entire; no undulation. Texture (upper side) — Glabrous and slightly velvety. Texture (under side) — Glabrous and slightly velvety. Luster (upper side) — Slightly glossy. Luster (under side) — Moderately glossy. Color when opening (upper side) — Red-purple, nearest to RHS 58C; veined darker, nearest to RHS 61C; margined red, nearest to in between RHS 37C and 37D. Color when opening (under side) — Red-purple, nearest to RHS 58B; veined darker, nearest to RHS 58A; margined red, nearest to in between RHS 37C and 37D. Color when fully opened (upper side) — Red-purple, nearest to RHS 64C; margined red, nearest to a mixture of RHS 39C and 39D. Color when fully opened (under side) — Red-purple, nearest to RHS 64C; margined red, nearest to a mixture of RHS 39C and 39D. Mature venation color (upper side) — Red-purple, nearest to RHS 67B. Mature venation color (under side) — Red-purple, nearest to a mixture of RHS 67A and 68B. Color when faded (upper side) — Red-purple, nearest to RHS 60B. Color when faded (under side) — Red-purple, nearest to RHS 60B.

Reproductive organs:
*Androecium*.—Stamen quantity — 9; occasionally 7. Filament — Length — 0.7 cm. Color — White, nearest to RHS NN155D, and fading to red-purple towards the distal end, nearest to RHS N74D. Anther — Attachment — Basifixed. Shape — Oblong. Dimensions — 0.1 cm long and 0.05 cm in diameter. Color — Greyed-orange, nearest to RHS 169A. Pollen — Amount of pollen — Moderately abundant. Pollen color — Yellow-orange, RHS 23A.
*Gynoecium*.—Pistil quantity — One. Length overall — 0.6 cm. Stigma — Shape — Cleft. Dimensions — Approximately 0.05 cm in diameter and 0.05 cm long. Color — White, nearest to RHS NN155B. Style — Dimensions — 0.55 cm long and 0.1 cm in diameter. Color — Red-purple, nearest to RHS 61D. Ovary — Color — Greyed-red, nearest to in between RHS 180C and 180D.

Seed and fruit: Not observed.

COMPARISONS WITH THE PARENT PLANTS AND CLOSEST KNOWN COMPARATOR

Plants of the new cultivar 'LOCORA3519' differ from the parents, *Lewisia cotyledon* '103500/A' (not patented), in the following characteristics described in Table 1 below.

TABLE 1

| Characteristic | 'LOCORA3519' | '103510/A' |
|---|---|---|
| Growth habit. | Rosette is more symmetrical than that of '103510/A', with uniform growth among all plants of any cultivated population. | Rosette is less symmetrical than that of 'LOCORA3519', with a degree of variability among plants of any cultivated population. |
| Plant vigor. | More vigorous than '103510/A', requiring only one growing season to produce a marketable plant in larger containers ranging in size from 12 to 15 cm. | Less vigorous than 'LOCORA3519', requiring two growing seasons to produce a marketable plant in smaller, 11 to 12 cm containers. |
| Flower size. | Larger than '103510/A'. | Smaller than 'LOCORA3519'. |
| Quantity of flowers per inflorescence. | More than '103510/A'. | Fewer than 'LOCORA3519'. |

COMPARISONS WITH THE CLOSEST KNOWN COMPARATOR

Plants of the new cultivar 'LOCORA3519' differ from the closest known commercial comparator, *Lewisia* 'Mountain Dreams' (not patented), in the following characteristics described in Table 2 below.

TABLE 2

| Characteristic | 'LOCORA3519' | 'Mountain Dreams' |
|---|---|---|
| Growth habit. | Uniform growth among all plants of any cultivated population. | Exhibits a degree of variability among plants of any cultivated population. |

TABLE 2-continued

| Characteristic | 'LOCORA3519' | 'Mountain Dreams' |
|---|---|---|
| Plant vigor. | More vigorous than 'Mountain Dreams', requiring only one growing season to produce a marketable plant in larger containers ranging in size from 12 to 15 cm. | Less vigorous than 'LOCORA3519', requiring two growing seasons to produce a marketable plant in smaller, 11 to 12 cm containers. |
| Vernalization requirement. | No vernalization requirement to induce flowering. | Plants require vernalization to induce flowering. |
| Uniformity of the corolla color. | Uniform and stable. | Highly variable. |

That which is claimed is:

1. A new and distinct variety of *Lewisia* plant named 'LOCORA3519', substantially as described and illustrated herein.

* * * * *